(12) United States Patent
Ahn

(10) Patent No.: US 9,498,403 B2
(45) Date of Patent: Nov. 22, 2016

(54) AUTOMATIC SALIVATION FACILITATING APPARATUS

(75) Inventor: Byeong-Cheol Ahn, Daegu (KR)

(73) Assignee: KYUNGPOOK NATIONAL UNIVERSITY INDUSTRY-ACADEMIC COOPERATION FOUNDATION (KR)

( * ) Notice: Subject to any disclaimer, the term of this patent is extended or adjusted under 35 U.S.C. 154(b) by 844 days.

(21) Appl. No.: 13/811,029

(22) PCT Filed: Jun. 2, 2011

(86) PCT No.: PCT/KR2011/004039
§ 371 (c)(1),
(2), (4) Date: Jan. 18, 2013

(87) PCT Pub. No.: WO2012/011661
PCT Pub. Date: Jan. 26, 2012

(65) Prior Publication Data
US 2013/0123677 A1    May 16, 2013

(30) Foreign Application Priority Data

Jul. 21, 2010 (KR) .................. 10-2010-0070416
Jun. 1, 2011 (KR) .................. 10-2011-0052841

(51) Int. Cl.
*A61H 7/00* (2006.01)
*A61H 15/00* (2006.01)
*A61H 23/02* (2006.01)
*A61M 31/00* (2006.01)

(52) U.S. Cl.
CPC .............. *A61H 7/007* (2013.01); *A61H 7/001* (2013.01); *A61H 15/0078* (2013.01);
(Continued)

(58) Field of Classification Search
CPC ............... A61H 2201/165; A61H 2201/1052; A61H 2201/1054; A61H 2201/1669; A61H 2201/1671; A61H 2201/1604; A61H 2201/16; A61H 11/00; A61H 11/02; A61H 15/00; A61H 2205/022; A61H 2205/026; A61H 7/00; A61H 7/001; A61H 7/002; A61H 7/004; A61H 7/006; A61H 7/007; A61H 2007/009; A61M 2005/3152; A61M 5/31583; A61M 5/31586
USPC ........................................................ 222/175
See application file for complete search history.

(56) References Cited

U.S. PATENT DOCUMENTS 733,398 A * 7/1903 Joseph ................... A61C 17/00
433/122
3,467,104 A * 9/1969 Burbridge ............. A61M 19/00
433/80

(Continued)

FOREIGN PATENT DOCUMENTS

KR   1020000037266    7/2000
KR   1020100002567    1/2010

OTHER PUBLICATIONS

International Search Report—PCT/KR2011/004039 dated Feb. 29, 2012.

*Primary Examiner* — Justine Yu
*Assistant Examiner* — Michael Tsai
(74) *Attorney, Agent, or Firm* — Cantor Colburn LLP

(57) ABSTRACT

Provided is an automatic salivation facilitating apparatus including a first parotid gland massaging device which massages user's one-side parotid gland, a second parotid gland massaging device which massages user's other-side parotid gland, a first fixing member which connects the first and second parotid gland massaging devices and allows the user to wear the automatic salivation facilitating apparatus, a salivation agent injection unit which is disposed to a lower portion of one of the first and second parotid gland massaging devices to periodically automatically inject salivation agent, and a controller which operates a main body. The automatic salivation facilitating apparatus utilizes a submandibular gland massaging device together with the salivation agent injection unit and the parotid gland massaging devices, so that the effect of facilitating salivation can be maximized.

13 Claims, 11 Drawing Sheets

(52) U.S. Cl.
CPC ....... *A61H 23/0254* (2013.01); *A61M 31/002* (2013.01); *A61H 2015/0042* (2013.01); *A61H 2201/105* (2013.01); *A61H 2201/1604* (2013.01); *A61H 2201/165* (2013.01); *A61H 2201/1607* (2013.01); *A61H 2201/1669* (2013.01); *A61H 2205/02* (2013.01); *A61H 2205/022* (2013.01); *A61H 2205/026* (2013.01)

(56) References Cited

U.S. PATENT DOCUMENTS

| | | | | |
|---|---|---|---|---|
| 4,820,506 A | * | 4/1989 | Kleinberg | A61K 33/42 424/40 |
| 5,611,771 A | * | 3/1997 | Taylor | A61H 23/0263 601/48 |
| 5,984,145 A | * | 11/1999 | McAllister | A45F 3/16 222/175 |
| 7,477,947 B2 | | 1/2009 | Pines et al. | |
| 2003/0009116 A1 | * | 1/2003 | Luettgen | A61H 19/34 601/46 |
| 2003/0009133 A1 | * | 1/2003 | Ramey | A61M 5/1456 604/155 |
| 2007/0179414 A1 | * | 8/2007 | Imboden | A61H 19/00 601/72 |
| 2008/0269648 A1 | * | 10/2008 | Bock | A61N 7/00 601/2 |
| 2010/0016908 A1 | * | 1/2010 | Martin | A61M 11/00 607/3 |

\* cited by examiner

AUTOMATIC SALIVATION FACILITATING APPARATUS

TECHNICAL FIELD

The present invention relates to a salivation facilitating apparatus, and more particularly, to an automatic salivation facilitating apparatus of automatically injecting a salivation agent to stimulate a parotid gland and a submandibular gland to facilitate salivation, so that toxins accumulated in a salivary gland can be effectively discharged.

BACKGROUND ART

The thyroid gland is a butterfly-shaped organ that is located below the thyroid cartilage in front of a bronchial tube as a respiratory air way. The thyroid gland has a function of producing and storing thyroid hormone and sending the thyroid hormone to organs which requires the hormones. Cancers occurring in thyroid are collectively called thyroid cancers. The thyroid cancers are mainly classified into "well-differentiated thyroid cancers' and "other thyroid cancers". In addition, the thyroid cancers are classified into papillary cancer, follicular cancer, medullary cancer, and anaplastic cancer (undifferentiated cancer) according to a histological shape, a source cell of cancer, and a degree of differentiation.

All the differentiated thyroid cancers are treated through thyroidectomy after diagnosis as possible. After the thyroidectomy, thyroid hormone is administered to suppress thyroid stimulating hormone (TSH), and the radioiodine therapy for full scanning using radioiodine and measuring serum thyroid globulin is periodically performed in order to easily observe recurrence and metastasis of the cancer. The radioiodine therapy has effects of assisting observation of the recurrence of the thyroid cancer, reducing a recurrence rate, and increasing lifetime of some patients.

However, the radioiodine administered into the body for the radioiodine therapy is also stored in the salivary gland and several organs such stomach. If the radioiodine is not speedily discharged from the body, the radioiodine therapy causes adverse effect such as salivary gland inflammation and radioactive inflammation of stomach. Particularly, the salivary gland is vulnerable to the radioiodine, and the damaged salivary gland is not nearly recovered. Therefore, in order to reduce the damage to the salivary gland caused by the radioiodine, it is important to remove the radioiodine from the salivary gland by facilitating the salivation. In the related art, a large amount of water is drunk or a candy or sour food is eaten so as to facilitate the salivation to discharge a large amount of saliva. However, in the above-described methods, the radioiodine cannot be completely removed. In addition, when the patient is in the sleep time, the above-described methods cannot be used, so that there is a limitation in effectively removing the radioiodine.

Korean Patent Application Publication No. 10-2000-0037266 discloses a salivation apparatus and method of manufacturing the same. The salivation apparatus is an apparatus which is fixed to teeth to facilitate salivation in order to solve the problem in the salivation. Although the Korean Patent Application Publication discloses only the method for stimulating the salivary gland located under the teeth, the method for directly removing radioiodine from the salivary gland is not disclosed. In addition, in the disclosed invention, since the mouth needs to be always opened, there is a problem in that moisture is evaporated so that the mouth becomes dry.

DISCLOSURE

Technical Problem

The present invention is to provide an automatic salivation facilitating apparatus capable of effectively removing radioiodine in a sleep time as well as in a non-sleep time by periodically injecting a salivation agent for salivation facilitation and by massaging a parotid gland and a submandibular gland which have the largest region among salivary glands.

Technical Solution

According to an aspect of the present invention, there is provided an automatic salivation facilitating apparatus including: a first parotid gland massaging device which is arranged so as to correspond to a left-side parotid gland of a user; a second parotid gland massaging device which is arranged so as to correspond to a right-side parotid gland of the user; a first fixing member which connects the first and second parotid gland massaging devices and allows the user to wear the automatic salivation facilitating apparatus; a salivation agent injection unit which is disposed to a lower portion of one of the first and second parotid gland massaging devices to periodically automatically inject a salivation agent; and a controller which includes a control unit which controls the first and second parotid gland massaging devices and the salivation agent injection unit and a power supply unit which supplies power to the first and second parotid gland massaging devices and the salivation agent injection unit.

In the automatic salivation facilitating apparatus according to the above aspect, the automatic salivation facilitating apparatus may further include a first submandibular gland massaging device which is arranged so as to correspond to a left-side submandibular gland of the user; a second submandibular gland massaging device which is arranged so as to correspond to a right-side submandibular gland of the user; and a second fixing member which connects the first and second submandibular gland massaging devices and allow the automatic salivation facilitating apparatus to be worn to a user's chin, wherein the first and second submandibular gland massaging devices are connected to the first and second parotid gland massaging devices, respectively, and are controlled to operate by the control unit.

In the automatic salivation facilitating apparatus according to the above aspect, each of the first and second parotid gland massaging devices may include: a first step motor; a conveyor which is connected to the first step motor to be moved in one direction according to driving of the first step motor; and a first massaging member which is fixed on a surface of the conveyor to be moved in one direction together with the conveyor.

In the automatic salivation facilitating apparatus according to the above aspect, the first massaging member may include: a connection bar of which the one side is connected to the surface of the conveyor; and a rotation ball which is disposed to the other side of the connection bar.

In the automatic salivation facilitating apparatus according to the above aspect, each of the first and second parotid gland massaging devices may further include a second step motor which is arranged between the first massaging member and the conveyor, the connection bar may be configured so that the one side thereof is connected to the second step motor, and the connection bar may be configured to be bent at a predetermined angle so that the other side thereof is circulated while rotating in a circle having a predetermined range by driving of the second step motor.

In the automatic salivation facilitating apparatus according to the above aspect, the connection bar may be configured with an elastic member, and the rotation ball may be formed in one of semispherical and spherical shapes.

In the automatic salivation facilitating apparatus according to the above aspect, the salivation agent injection unit may include: a salivation agent syringe which is configured to include a cylinder which contains a salivation agent and where an outlet for ejecting the salivation agent is formed at the one side thereof and a plunger which is moved along an inner side of the cylinder; a third step motor; a gear mechanism which is configured to include a primary gear which is connected to the third step motor and a plurality of secondary gears which are moved in engagement with the primary gear; a plunger moving screw which is rotated in connecting to the last secondary gear in the gear mechanism; a plunger gasket which is disposed in an inner portion of the cylinder of the salivation agent syringe and disposed to the one side of the plunger to adjust an internal pressure of the cylinder according to the movement the plunger gasket; and a plunger fastening nut which is disposed to the other side of the plunger opposite to the plunger gasket and is moved in engagement with the rotation of the plunger moving screw to move the plunger, so that the salivation agent injection amount can be adjusted.

In the automatic salivation facilitating apparatus according to the above aspect, the salivation agent injection unit may include a salivation agent injection tube of which the one side is connected to the outlet of the salivation agent syringe and of which the other side is disposed in a user's oral cavity and which is configured with a flexible material.

In the automatic salivation facilitating apparatus according to the above aspect, the salivation agent injection unit may further include an injection tube fastening member which fastens the salivation agent injection tube to the user's oral cavity, and which the injection tube fastening member is fixed to user's teeth.

In the automatic salivation facilitating apparatus according to the above aspect, each of the first and second submandibular gland massaging devices may include: a fourth step motor; a rotation plate which is rotated in connection to the fourth step motor; a second massaging member which massages a submandibular gland; and a connection member of which the one side is connected to a position shifted from the center of the rotation plate and of which the other side is connected to the second massaging member.

In the automatic salivation facilitating apparatus according to the above aspect, the control unit may further include an external setting unit which can set operation conditions externally, and the control unit may be operated according to the conditions set by the external setting unit.

In the automatic salivation facilitating apparatus according to the above aspect, the automatic salivation facilitating apparatus may further include a third fixing member which connects the first and second parotid gland massaging devices and is disposed at a predetermined angle with respect to the first fixing member.

In the automatic salivation facilitating apparatus according to the above aspect, each of the first and second parotid gland massaging devices may include: a plurality of piston units which are aligned in one direction; and a plurality of first massaging members which are fixed to the respective piston units to perform a reciprocating motion forwards by driving of the piston units, and the control unit may control the piston units to sequentially perform the reciprocating motion.

In the automatic salivation facilitating apparatus according to the above aspect, the piston units may be systematically connected to each other, so that the piston units are driven by using one first step motor or so that the piston units are separately driven by the respective first step motors.

In the automatic salivation facilitating apparatus according to the above aspect, each of the first massaging members may include: a connection bar of which the one side is connected to a surface of the piston unit; and a rotation ball which is disposed to the other side of the connection bar.

In the automatic salivation facilitating apparatus according to the above aspect, each of the first and second parotid gland massaging devices may further include a first contact portion which is disposed in front of the first massaging member and is configured with a disposable cover made of a waterproof material so that the first contact portion is replaced after the use of the automatic salivation facilitating apparatus.

In the automatic salivation facilitating apparatus according to the above aspect, the connection bar may be configured with an elastic member, and the rotation ball may be formed in one of semispherical and spherical shapes.

Advantageous Effects

The automatic salivation facilitating apparatus according to the present invention includes a salivation agent injection unit which periodically automatically injects a salivation agent, so that it is possible to minimize a staying time of toxins in a salivary gland by periodically injecting the salivation agent in the sleep time and it is possible to obtain periodic salivation and saliva discharging even in the non-sleep time.

In addition, the automatic salivation facilitating apparatus according to the present invention includes massaging devices for massaging a parotid gland and a submandibular gland, so that it is possible to effectively discharge toxins stored in the salivary gland by facilitating salivation.

In addition, the automatic salivation facilitating apparatus according to the present invention massages a parotid gland in one direction, so that toxins are prevented from being stored in the body but the toxins are allowed to be easily discharged.

In addition, the automatic salivation facilitating apparatus according to the present invention utilizes a submandibular gland massaging device together with a salivation agent injection unit and a parotid gland massaging device, so that the effect of facilitating the salivation can be maximized. As a result, the automatic salivation facilitating apparatus according to the present invention can be used for a variety of disease requiring continuous salivation as well as for removing radioiodine from the salivary gland. In addition, the automatic salivation facilitating apparatus according to the present invention can be used for maintaining the functions of the salivary gland by continuously stimulating the salivary gland and can be used for preventing and treating disease of the oral cavity and teeth caused by a decrease in the salivation.

On the other hand, the automatic salivation facilitating apparatus according to the present invention includes an external setting unit so that a salivation agent injection period, a massaging time and interval can be adjusted, and thus, it is possible to effectively toxins from the salivary gland with optimal conditions according to an individual person.

In addition, the automatic salivation facilitating apparatus according to the present invention includes several fixing members, so that the automatic salivation facilitating apparatus can be stably fixed in the using time and can be comfortably worn by the user without separation from the user in the sleep time.

BEST MODE

Hereinafter, structures and operational principles of automatic salivation facilitating apparatuses according to exemplary embodiments will be described in detail with reference to the attached drawings.

First Embodiment

Figure 1:
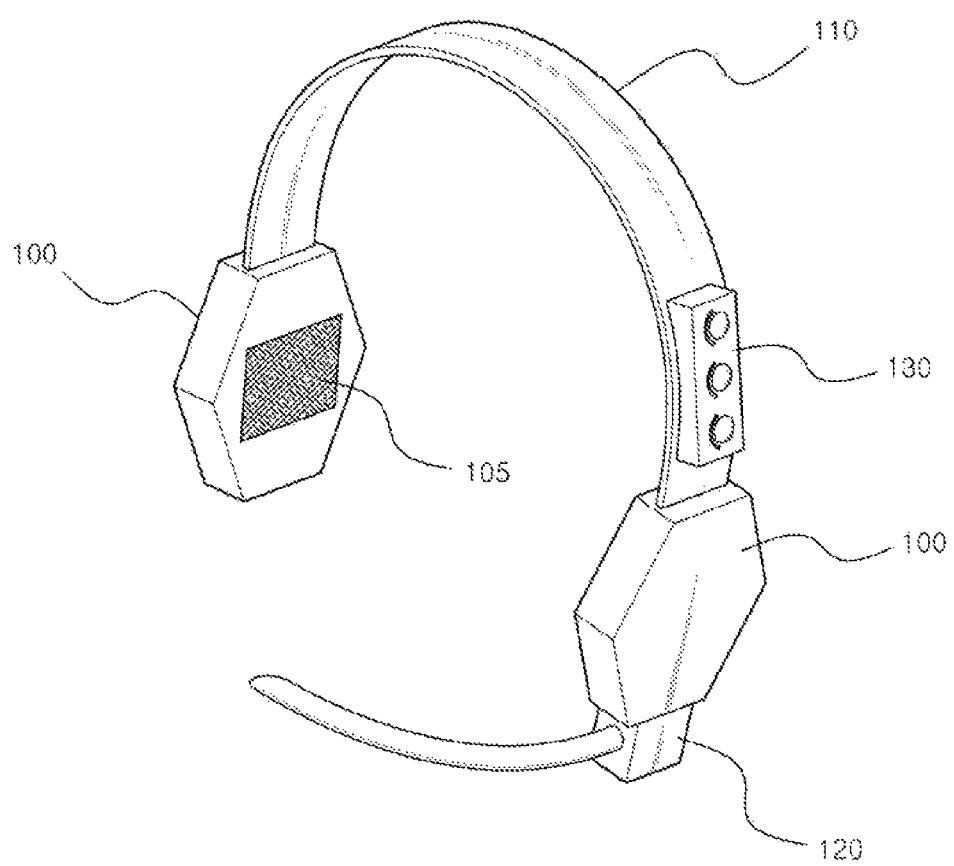
FIG. 1 is a schematic diagram illustrating an automatic salivation facilitating apparatus according to a first embodiment of the present invention.

FIG. 1 is a schematic diagram illustrating an automatic salivation facilitating apparatus according to a first embodiment of the present invention. Referring to FIG. 1, the automatic salivation facilitating apparatus according to the first embodiment of the present invention is configured to include a first parotid gland massaging device 100, a second parotid gland massaging device 100, a first fixing member 110, a salivation agent injection unit 120, and a controller 130.

The first and second parotid gland massaging device 100 massages two parotid glands of a user. The first fixing member 110 connects the first and second parotid gland massaging devices 100, which are disposed to massage the two parotid glands of the user, to each other and allows the user to wear the automatic salivation facilitating apparatus. The salivation agent injection unit 120 is disposed to a lower portion of one of the first and second parotid gland massaging devices to periodically automatically inject a salivation agent. The controller 130 is configured to include a control unit 132 which controls the first and second parotid gland massaging devices and the salivation agent injection unit as components of the automatic salivation facilitating apparatus and a power supply unit 134 which supplies power to the first and second parotid gland massaging devices and the salivation agent injection unit as components of the automatic salivation facilitating apparatus.

Figure 2A:
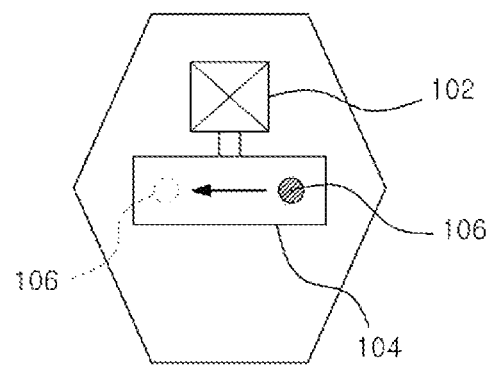
FIGS. 2A to 2D are schematic diagrams illustrating a structure of a first parotid gland massaging device according to the first embodiment of the present invention.

Hereinafter, structures and operational principles of the first and second parotid gland massaging devices 100 and the salivation agent injection unit 120 will be described in detail with reference to the drawings. First, the first and second parotid gland massaging devices 100 are described. The first and second parotid gland massaging devices have the same structure and operational principle, and thus, only one thereof will be described. FIGS. 2A to 2D are schematic diagrams illustrating a structure of a first parotid gland massaging device according to the first embodiment of the present invention. Referring to FIG. 2A, the first parotid gland massaging device 100 of the automatic salivation facilitating apparatus according to the present invention is configured to include a first step motor 102, a conveyor 104, and a first massaging member 106.

The conveyor 104 is connected to the first step motor 102 at the center thereof, so that the conveyor is moved in one direction to operate according to driving of the first step motor 102. On the other hand, in order to increase operation efficiency of the conveyor 104, the parotid gland massaging device 100 may include one or more step motors. In the case where the parotid gland massaging device includes one step motor, it is preferable that the one step motor is disposed at the center of the conveyor 104 to operate the conveyor 104 to rotate. In the case where the parotid gland massaging device includes at least two step motors, it is preferable that the step motors are disposed at positions so that the conveyor 104 can be efficiently operated.

Figure 2B:
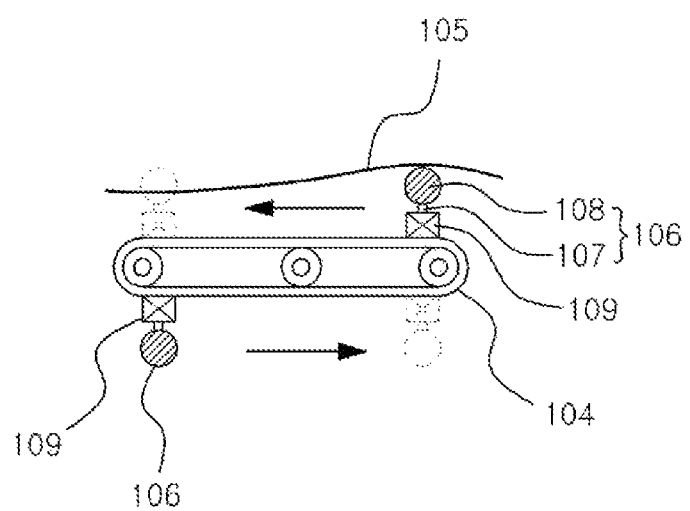

The first massaging member 106 is fixed on a surface of the conveyor 104 to be moved in one direction according to the operation of the conveyor 104, so that the first massaging member 106 massages the parotid gland. Referring to FIG. 2B, the first massaging member 106 is configured to include a connection bar 107 of which the one side is connected to the surface of the conveyor 104 and a rotation ball 108 which is disposed at the other side of the connection bar 107. On the other hand, the first parotid gland massaging device 100 is configured so that at least two first massaging members 106 are disposed in a predetermined interval on the surface of the conveyor, so that massage can be effectively performed. Since the conveyor 104 does not perform a reciprocating motion but performs a straight-line motion in one direction, in comparison with one massaging member is included, in the case where at least two massaging members are included, it is possible to effectively perform a larger amount of massaging within the same time.

Figure 2C:
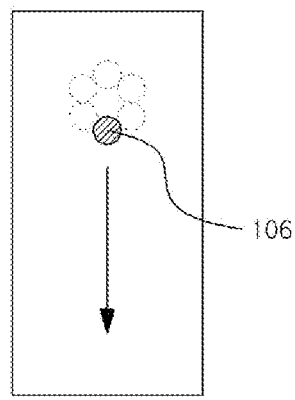

In addition, the first parotid gland massaging device 100 further includes a second step motor 109 between the first massaging member 106 and the conveyor. The connection bar 107 of the first massaging member 106 is configured so that the one side of the connection bar 107 is connected to the second step motor 109, and the connection bar 107 is configured to be bent at a predetermined angle so that the other side thereof is circulated while rotating in a circle having a predetermined range by the driving of the second step motor 109. Referring to FIG. 2C, it can be understood that the first massaging member 106 is moved in one direction while rotating in a circle having a predetermined range. The movement of the first massaging member 106 further stimulates the parotid gland, so that the salivation facilitation can be maximized.

In addition, it is preferable that the connection bar 107 is configured with an elastic member so as not to exert an excessive stimulus on the face, and when the rotation ball 108 is in close contact with the face, the connection bar 107 is bent and moved in accordance with the face, so that the parotid gland can be massaged with an appropriate force. In addition, it is preferable that the rotation ball 108 is formed in a semispherical or spherical shape so as to smoothly massage the face.

Figure 2D:
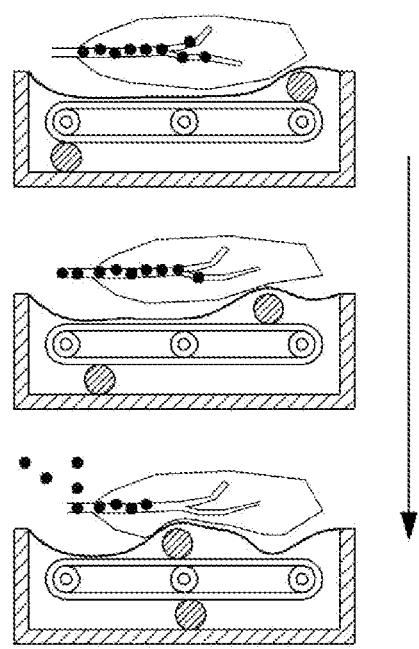

Referring to FIG. 2D, the parotid gland massaging device 100 of the automatic salivation facilitating apparatus having the above-described configuration according to the present invention is simply moved in one direction or is moved in one direction while rotating in a circle having a predetermined range. Therefore, the toxins stored in the parotid gland is prevented from being flowed into the body and is discharged. In addition, the parotid gland is stimulated to facilitate the salivation, so that the toxins can be effectively discharged into the oral cavity. In addition, since the parotid gland is the largest salivary gland among the human salivary glands, toxins can be more effectively removed by massaging the parotid gland than by massaging other salivary glands.

On the other hand, the first parotid gland massaging device 100 may further includes a first contact portion 105 which is disposed in front of the first massaging members 106. The first contact portion 105 needs to minimize the stimulus exerted on the face by the motion of the first massaging members 106 and needs to allow the first massaging members 106 to smoothly be moved. In addition, since radioiodine may be discharged in form of saliva and sweat, the first contact portion 105 which is in direct contact with a patient's skin may be contaminated with radioactivity, so that the reuse of the first contact portion 105 is restricted. Therefore, the first contact portion 105 is configured with a disposable cover made of a waterproof material, so that the first contact portion 105 can be replaced after the use of automatic salivation facilitating apparatus according to the present invention.

Next, the salivation agent injection unit 120 will be described.

Figure 3A:
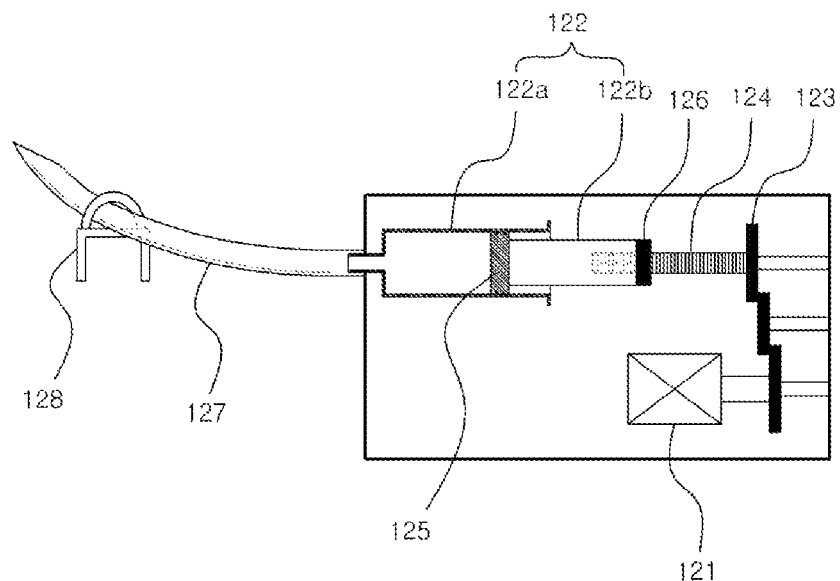
FIGS. 3A and 3B are schematic diagrams illustrating a structure of a salivation agent injection unit of the automatic salivation facilitating apparatus according to the first embodiment of the present invention.
Figure 3B:
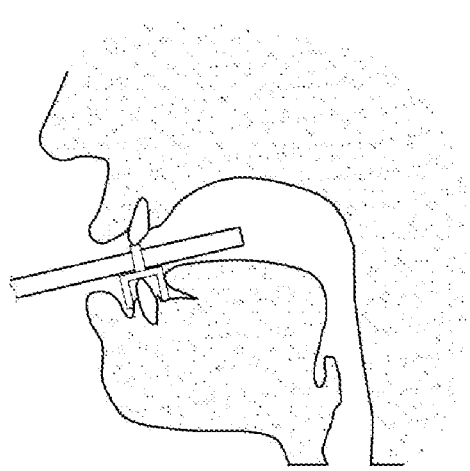

FIGS. 3A and 3B are schematic diagrams illustrating a structure of a salivation agent injection unit of the automatic salivation facilitating apparatus according to the first embodiment of the present invention. Referring to FIG. 3A, the salivation agent injection unit 120 is configured to include a third step motor 121, a salivation agent syringe 122, a gear mechanism 123, a plunger moving screw 124, a plunger gasket 125, and a plunger fastening nut 126.

The salivation agent syringe 122 is configured to include a cylinder 122a which contains a salivation agent and where an outlet for ejecting the salivation agent is formed at the one side thereof and a plunger 122b which is moved along the inner side of the cylinder 112a. On the other hand, a salivation agent injection tube 127 of which the one side is connected to the outlet of the salivation agent syringe 122 and of which the other side is disposed in the user's oral cavity is disposed to the outlet of the salivation agent syringe 122 so that the salivation agent can be accurately injected into the user's oral cavity. The salivation agent injection tube 127 is configured with a flexible, harmless material. In this embodiment, silicon may be used. In addition, the salivation agent injection unit according to the present invention may further include an injection tube fastening member 128 which can fasten the salivation agent injection tube 127. The injection tube fastening member 128 fastens the salivation agent injection tube 127 so as to be accurately positioned in the oral cavity when the user is in the sleep time or in the non-sleep time. In this case, the distal end of the injection tube is allowed to be positioned at the portion sensing a vinegary taste, so that it I possible to maximize the effect of the salivation agent. Referring to FIG. 3B, in the present invention, the injection tube fastening member 128 may be fixed to the user's teeth so as to fasten the injection tube.

The gear mechanism 123 is configured to include a primary gear which is connected to the third step motor 121 and a plurality of secondary gears which are moved in engagement with the primary gear. The plunger moving screw 124 is rotated in connection to the last secondary gear in the gear mechanism 123. The last secondary gear is a secondary gear which has no gear moved by the secondary gear, among the secondary gears which are moved in engagement with the rotation of the primary gear connected to the third step motor 121.

The plunger gasket 125 is disposed in the inner portion of the cylinder 122a of the salivation agent syringe 122 and disposed to the one side of the plunger 122b. According to the movement of the plunger gasket 125, the internal pressure of the cylinder 122a can be adjusted. The plunger fastening nut 126 is disposed to the other side of the plunger 122b opposite to the plunger gasket 125 and is moved in engagement with the rotation of the plunger moving screw 124 to move the plunger 122b, so that the salivation agent injection amount can be adjusted.

Hereinbefore, the parotid gland massaging device 100 and the salivation agent injection unit 120 of the automatic salivation facilitating apparatus according to the first embodiment of the present invention were described in detail. Hereinafter, the structure of the automatic salivation facilitating apparatus including the parotid gland massaging device 100 and the salivation agent injection unit 120 will be described in detail.

The first and second parotid gland massaging devices 100 having the above-described configuration are disposed to the positions corresponding to the left-side and right-side parotid glands so as to massage the user's parotid glands, and the first and second parotid gland massaging devices are fixed by a first fixing member 110. Since the users are different in size of head and the fixing positions thereof are different according to the users' preference, the first fixing member 110 is configured so that the first fixing member 110 can be deformed. In addition, the first fixing member 100 may include wire lines which connect the controller 130 and the power supply unit 140 to the first and second parotid gland massaging devices 100 and the salivation agent injection unit 120.

Figure 4:
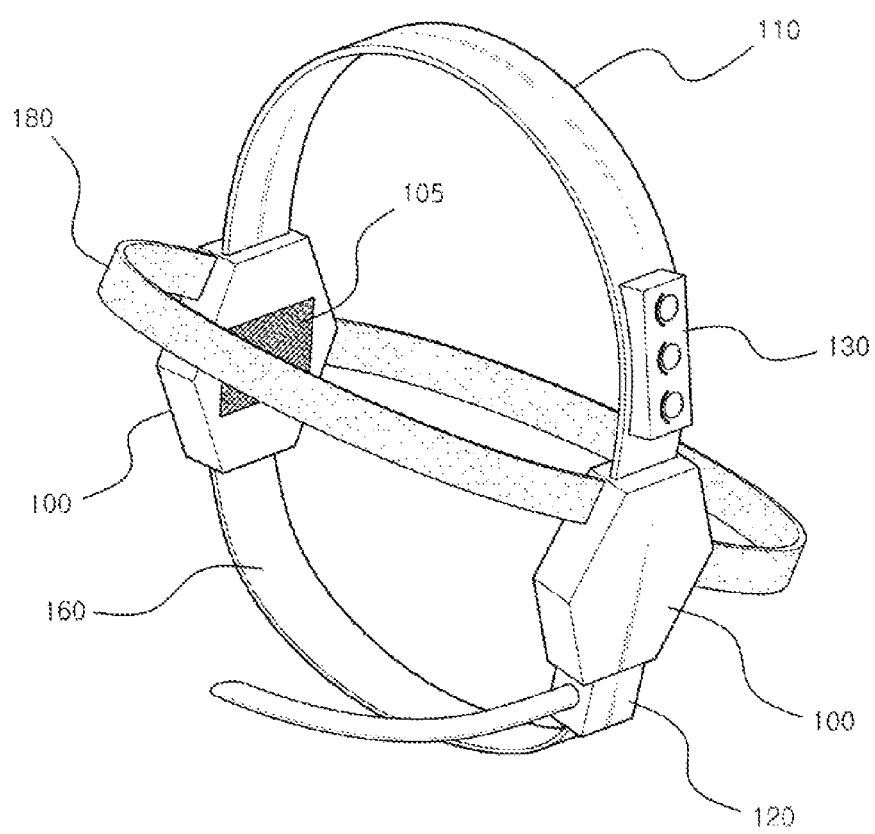
FIG. 4 is a diagram illustrating an example where the automatic salivation facilitating apparatus according to the first embodiment of the present invention is worn.

In addition, due to the user's movement in the sleep time, the automatic salivation facilitating apparatus may not be fixed but separated from the user. Therefore, in order to fix the automatic salivation facilitating apparatus, the automatic salivation facilitating apparatus may additionally include a second fixing member 160 and a third fixing member 180. FIG. 4 is a diagram illustrating an example where the automatic salivation facilitating apparatus according to the first embodiment of the present invention is worn. The second fixing member 160 is connected to the main body. More specifically, the second fixing member 160 is connected to the other side of the main body opposite to the one side thereof connected to the first fixing member 110. In the case where the user wears the first fixing member 110 on the user's head, the second fixing member 160 may be worn so as to prop the chin. The third fixing member 180 is an auxiliary fixing member which is allowed to completely fix the automatic salivation facilitating apparatus according to the present invention. The third fixing member 180 may be worn so as to surround the user's head. Similarly to the first fixing member 110, the second fixing member 160 and the third fixing member 180 are configured so that the second fixing member 160 and the third fixing member 180 can be deformed in accordance with the user's head.

Figure 5A:
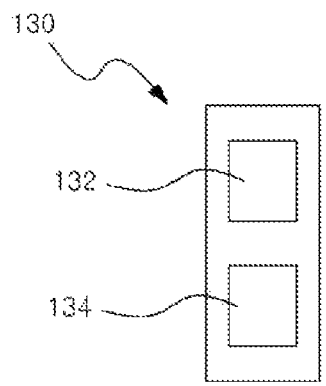
FIGS. 5A and 5B are a schematic diagram illustrating a structure of a controller of the automatic salivation facilitating apparatus according to the first embodiment of the present invention.
Figure 5B:
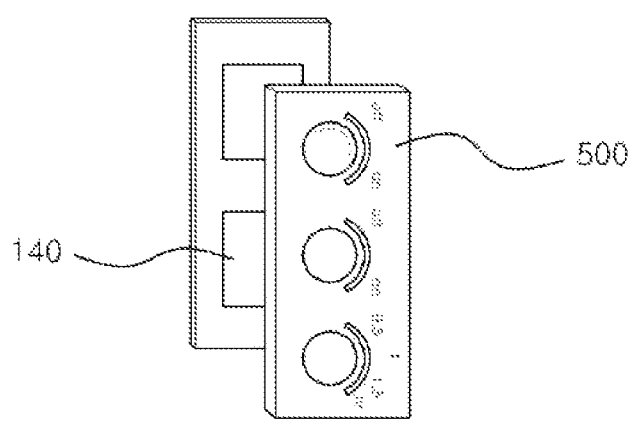

FIGS. 5A and 5B are schematic diagrams illustrating a structure of a controller of the automatic salivation facilitating apparatus according to the first embodiment of the present invention. Referring to FIG. 5A, the controller 130 is configured to include a control unit 132 which controls components of the automatic salivation facilitating apparatus and a power supply unit 134 which supplies power to the components of the automatic salivation facilitating apparatus. The controller 130 can control salivation facilitating conditions such as a massaging period, a one-massaging time, a salivation agent injection amount, and a salivation agent injection period. In addition, referring to FIG. 5B, the controller 130 may further include an external setting unit 500 through which the user can directly input the conditions described above.

The automatic salivation facilitating apparatus having the above-described configuration according to the first embodiment of the present invention periodically automatically massages the parotid gland in the non-sleep time as well as in the sleep time, so that the toxins stored in the salivary gland can be discharged in a short time. In addition, since the massaging is performed so as to push the toxins out in one direction, the toxins cannot be flowed into the body but discharged. The salivation agent as a material for facilitating the salivation is periodically automatically injected, so that it is possible to more effectively remove the toxins through the massaging.

Second Embodiment

Hereinafter, structures and operational principles of an automatic salivation facilitating apparatus according to a second embodiment of the present invention will be described in detail with reference to the attached drawings. Although the structure of the automatic salivation facilitating apparatus according to the second embodiment is similar to that of the automatic salivation facilitating apparatus according to the first embodiment, the automatic salivation facilitating apparatus according to the second embodiment further includes first and second submandibular gland massaging devices.

Figure 6:
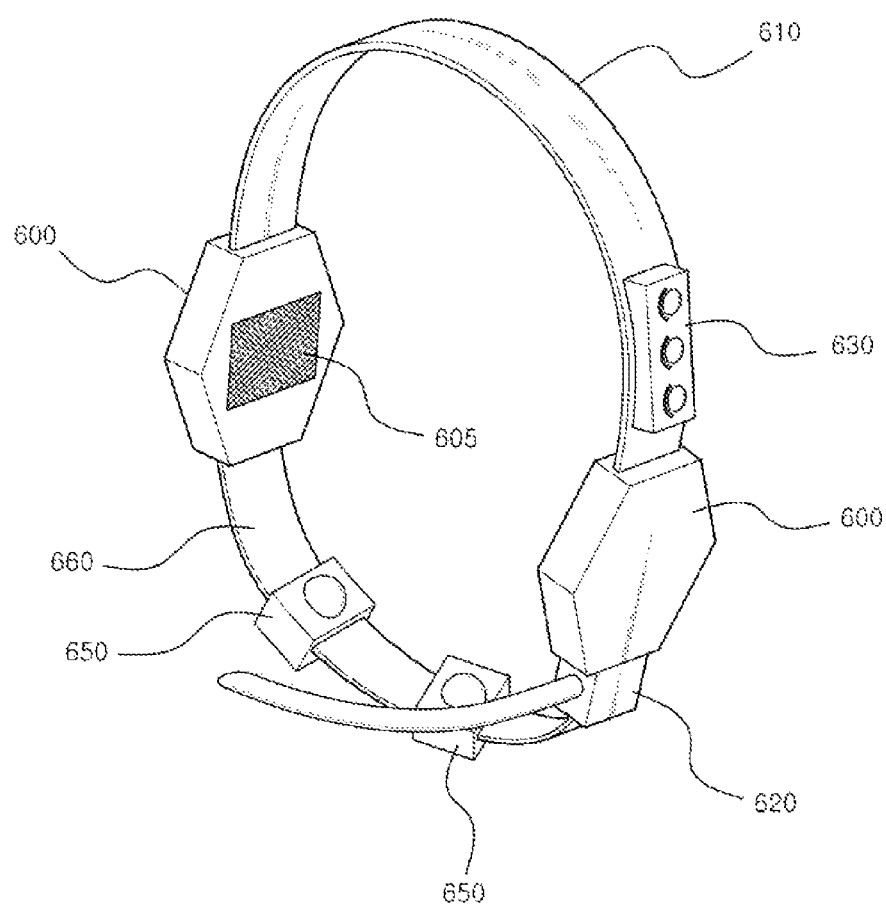
FIG. 6 is a schematic diagram illustrating an automatic salivation facilitating apparatus according to a second embodiment of the present invention.

FIG. 6 is a schematic diagram illustrating an automatic salivation facilitating apparatus according to the second embodiment of the present invention. Referring to (a) of FIG. 6, the automatic salivation facilitating apparatus according to the second embodiment of the present invention is configured to include a first parotid gland massaging device 600, a second parotid gland massaging device 600, a first fixing member 610, a salivation agent injection unit 620, a controller 630, a second fixing member 660, and first and second submandibular gland massaging devices 650. The components of the second embodiment are the same as those of the first embodiment except for the submandibular gland massaging devices 650, and thus, description of the same components is omitted.

Figure 7:
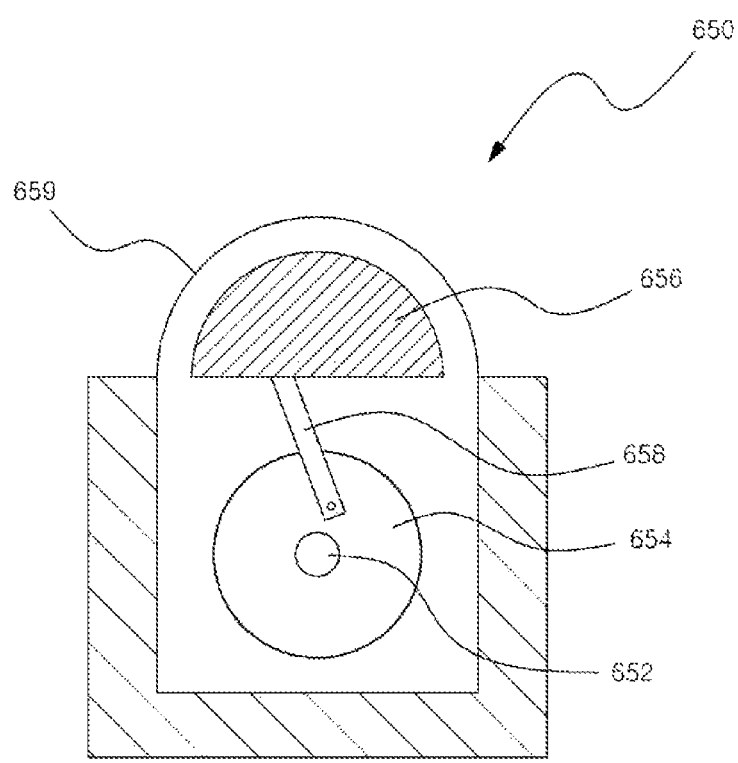
FIG. 7 is a schematic diagram illustrating a structure of a first submandibular gland massaging device of the automatic salivation facilitating apparatus according to the second embodiment of the present invention.

FIG. 7 is a schematic diagram illustrating a structure of a first submandibular gland massaging device of the automatic salivation facilitating apparatus according to the second embodiment of the present invention. Since the first and second submandibular gland massaging devices 650 have the same structure and operational principle, only one thereof will be described. Referring to FIG. 7, the first submandibular gland massaging device 650 according to the second embodiment is configured to include a fourth step motor 652, a rotation plate 654, a second massaging member 656, and a connection member 658.

The rotation plate 654 is rotated in connection to the fourth step motor 652.

The second massaging member 656 is arranged at the position corresponding to the submandibular gland to massage the submandibular gland. The one side of the connection member 658 is connected to a position shifted from the center of the rotation plate 654, and the other side of the connection member 658 is connected to the second massaging member 656. When the rotation plate 654 is rotated by the fourth step motor 652, the one side of the connection member performs rotation motion, and the other side of the connection member which is connected to the second massaging member 656 performs a straight line motion. Therefore, the second massaging member 656 repeats up and down motions to perform massage to stimulate the user's submandibular gland.

Two submandibular gland massaging devices 650 are installed so as to massage user's two submandibular glands, and the two submandibular gland massaging devices are connected to each other by a second fixing member 660 as a fixing member which props the chin. The other sides of the first and second submandibular gland massaging devices 650, which are not connected to the second fixing member 640, are connected to the first and second parotid gland massaging devices, and the first and second submandibular gland massaging devices 650 are controlled by the control unit to be operated.

On the other hand, the submandibular gland massaging device 650 may further include a second contact portion 659 which is disposed in front of the second massaging member 656. The second contact portion 659 needs to minimize the stimulus exerted on the face through the massaging of the second massaging member 656. In addition, since radioiodine may be discharged in form of saliva and sweat, the second contact portion 659 which is in direct contact with a patient's skin may be contaminated with radioactivity, so that the reuse of the second contact portion 659 is restricted. Therefore, the second contact portion 659 is configured with a disposable cover made of a waterproof material, so that the second contact portion 659 can be replaced after the use of automatic salivation facilitating apparatus according to the present invention.

Figure 8:
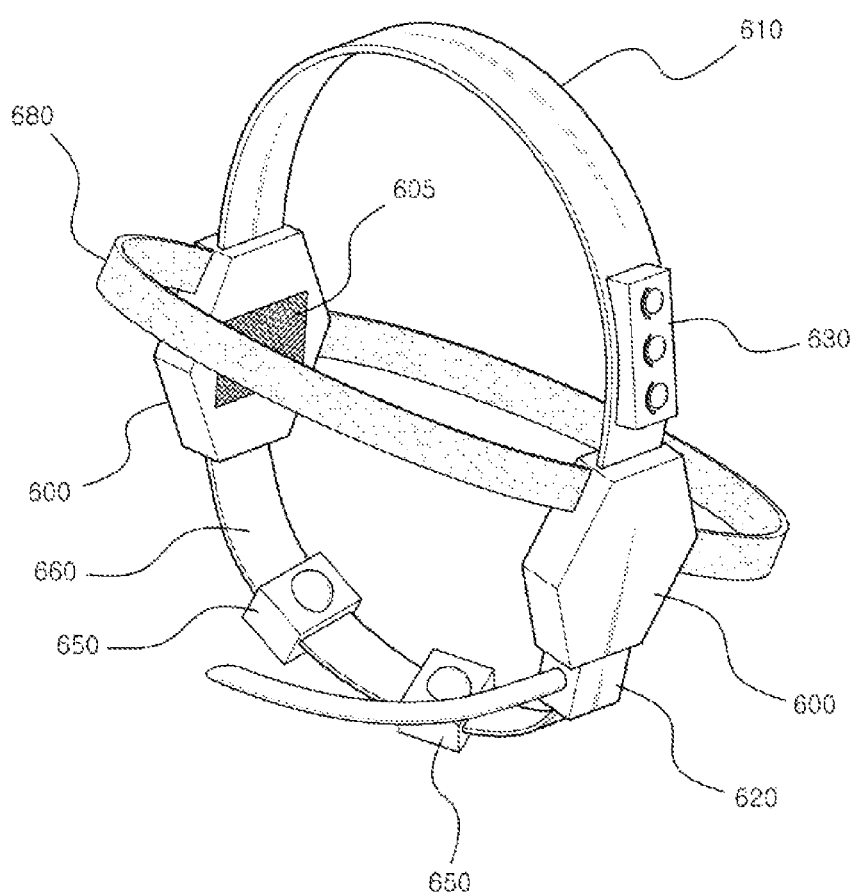
FIG. 8 is a diagram illustrating an example where the automatic salivation facilitating apparatus according to the second embodiment of the present invention is worn.

FIG. 8 is a diagram illustrating an example where the automatic salivation facilitating apparatus according to the second embodiment of the present invention is worn. Referring to FIG. 8, since the automatic salivation facilitating apparatus having the above-described configuration according to the second embodiment further includes the submandibular gland massaging device, salivation can be additionally improved in addition to the salivation performed by the automatic salivation facilitating apparatus according to the first embodiment, so that it is possible to effectively discharge toxins from the salivary gland.

Third Embodiment

Hereinafter, structures and operational principles of an automatic salivation facilitating apparatus according to a third embodiment of the present invention will be described in detail with reference to the attached drawings. Although the structure of the automatic salivation facilitating apparatus according to the third embodiment is similar to those of the first and second embodiments, the first and second parotid gland massaging devices according to the third embodiment are different from the first and second parotid gland massaging devices using conveyors according to the first and second embodiments in that the first and second parotid gland massaging devices according to the third embodiment use piston units to massage parotid glands. Therefore, the first and second parotid gland massaging devices of the automatic salivation facilitating apparatus according to the third embodiment, which have different features from the first and second embodiments, will be mainly described. In addition, the first and second parotid gland massaging devices have the same structure and operational principle, and thus, only one thereof will be described.

Figure 9A:
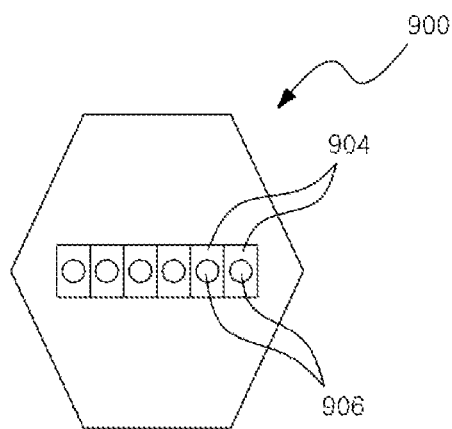
FIGS. 9A, 9B and 9C are schematic diagrams illustrating a structure of a first parotid gland massaging device according to a third embodiment of the present invention.
Figure 9B:
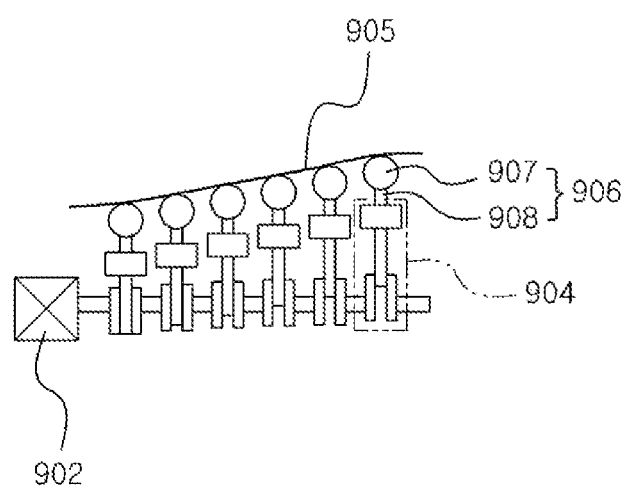
Figure 9C:
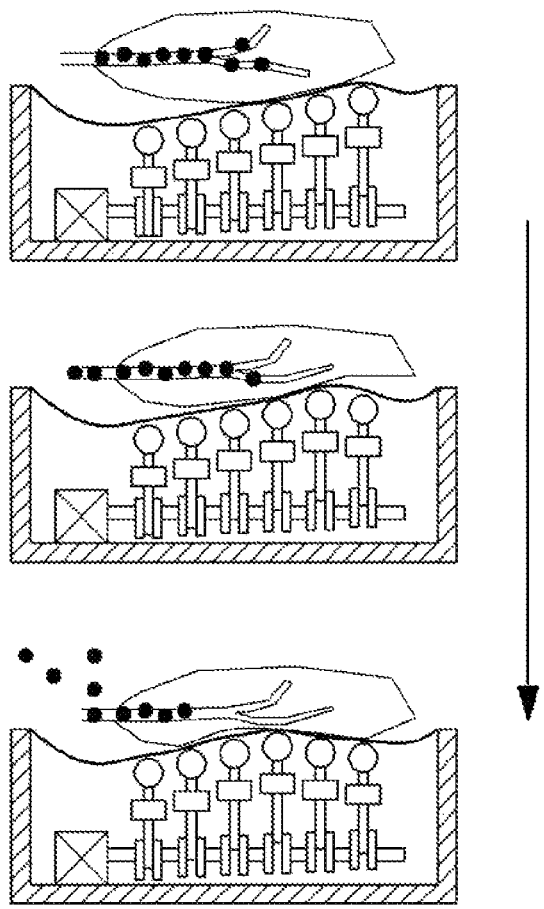

FIGS. 9A to 9C are schematic diagrams illustrating a structure of a first parotid gland massaging device according to the third embodiment of the present invention. Referring to FIG. 9A, the first parotid gland massaging device 900 of the automatic salivation facilitating apparatus according to the third embodiment of the present invention is configured to include a plurality of piston units 904 and a plurality of first massaging members 906.

The piston units 904 are aligned in one direction. The piston units 904 which are aligned in one direction is controlled by the control unit so as to be sequentially perform a reciprocating motion. At this time, the piston units 904 are systematically connected to each other, so that the piston units 904 can be driven by one first step motor 902. Referring to FIG. 9B, the piston units 904 are systematically connected to a shaft connected to the first step motor 902, and thus, although the only one first step motor is controlled, the piston units 904 sequentially performs the reciprocating motion. On the other hand, the piston units 904 may be configured to be individually driven by respective first step motors. In this embodiment, the configuration where the piston units 904 are driven by the one first step motor described above will be described.

The first massaging members 906 are fixed to the respective piston units 904. Therefore, the first massaging members 906 perform the reciprocating motion forwards by the driving of the respective piston units 904. Referring to FIG. 9C, the piston units 904 sequentially perform the reciprocating motion in the direction from the user's parotid gland to the front of the face, so that the first massaging members fixed to the piston units sequentially push and massage the parotid gland. Therefore, the toxins stored in the parotid gland is prevented from being flowed into the body and is discharged. In addition, the parotid gland is stimulated to facilitate the salivation, so the toxins can be effectively discharged into the oral cavity.

On the other hand, referring to FIG. 9B, the first massaging member 906 is configured to include a connection bar 907 of which the one side is connected to the surface of the piston unit 904 and a rotation ball 908 which is disposed to the other side of the connection bar 907. In addition, it is preferable that the connection bar 907 is configured with an elastic member so as not to exert an excessive stimulus on the face, and when the rotation ball 908 is in close contact with the face, the connection bar 907 is bent and moved in accordance with the face, so that the parotid gland can be massaged with an appropriate force. In addition, it is preferable that the rotation ball 908 is configured in a semi-spherical or spherical shape so as to smoothly massage the face.

In the automatic salivation facilitating apparatus having the above-described configuration according to the present invention, the parotid gland massaging device 900 uses the piston units which simply perform the reciprocating motion to allow the first massaging members to be moved to sequentially push the parotid gland, so that it is possible to obtain the same effect of discharging the toxins stored in the parotid gland as those of the first and second embodiments.

On the other hand, the first parotid gland massaging device 900 may further includes a first contact portion 905 which is disposed in front of the first massaging members 906. The first contact portion 905 needs to minimize the stimulus exerted on the face by the motion of the first massaging members 906 and needs to allow the first massaging members 906 to smoothly be moved. In addition, since radioiodine may be discharged in form of saliva and sweat, the first contact portion 905 which is in direct contact with a patient's skin may be contaminated with radioactivity, so that the reuse of the first contact portion 905 is restricted. Therefore, the first contact portion 905 is configured with a disposable cover made of a waterproof material, so that the first contact portion 905 can be replaced after the use of automatic salivation facilitating apparatus according to the present invention.

While the present invention has been particularly shown and described with reference to exemplary embodiments thereof, it will be understood by those skilled in the art that various changes in form and details may be made therein without departing from the spirit and scope of the invention as defined by the appended claims. The exemplary embodiments should be considered in descriptive sense only and not for purposes of limitation. Therefore, the scope of the invention is defined not by the detailed description of the invention but by the appended claims, and all differences within the scope will be construed as being included in the present invention.

INDUSTRIAL APPLICABILITY

An automatic salivation facilitating apparatus according to the present invention can be widely used in all the fields where medical treatment is performed through salivation facilitation. Although the present invention is disclosed so as to prevent damage of the salivary gland and protect the functions of the salivary gland by effectively removing radioiodine used for thyroid cancer treatment from the salivary gland, the present invention may be used for removing other toxins from the salivary gland through the salivation or for a variety of disease requiring continuous salivation. Due to aging or the like, the functions of the salivary gland are weakened. Accordingly, xerostama may occur. At this time, the automatic salivation facilitating apparatus according to the present invention can be used for stimulating the salivary gland to maintain the functions of the salivary gland. In addition, the automatic salivation facilitating apparatus according to the present invention can be used for preventing xerostama in advance and relaxing the deterioration in the functions of the salivary gland. In addition, the automatic salivation facilitating apparatus according to the present invention can be used for preventing and treating disease of the oral cavity and teeth caused by a decrease in the salivation.

The invention claimed is:

1. An automatic salivation facilitating apparatus comprising:
   a first parotid gland massaging device which is arranged so as to correspond to a left-side parotid gland of a user;
   a second parotid gland massaging device which is arranged so as to correspond to a right-side parotid gland of the user;
   a first fixing member which connects the first and second parotid gland massaging devices and allows the user to wear the automatic salivation facilitating apparatus, wherein each of the first and second parotid gland massaging devices includes: a first step motor; a conveyor which is connected to the first step motor to be moved in one direction according to driving of the first step motor; and a first massaging member which is fixed on a surface of the conveyor to be moved in one direction together with the conveyor;
   a salivation agent injection unit which is connected to a lower portion of one of the first and second parotid gland massaging devices to periodically automatically inject a salivation agent; and
   a controller which includes a control unit and a power supply unit which supplies power to the first and second parotid gland massaging devices and the salivation agent injection unit,
   wherein the control unit is configured to control the first and second parotid gland massaging devices and the salivation agent injection unit according to salivation facilitating conditions including a massaging period, a massaging time, a salivation agent injection amount and a salivation agent injection period to effectively remove toxins through massaging by injecting periodically the salivation agent.

2. The automatic salivation facilitating apparatus according to claim 1, further comprising:
   a first submandibular gland massaging device which is arranged so as to correspond to a left-side submandibular gland of the user;
   a second submandibular gland massaging device which is arranged so as to correspond to a right-side submandibular gland of the user; and
   a second fixing member which connects the first and second submandibular gland massaging devices and allow the automatic salivation facilitating apparatus to be worn to a user's chin,
   wherein the first and second submandibular gland massaging devices are connected to the first and second parotid gland massaging devices, respectively, and are controlled to operate by the control unit.

3. The automatic salivation facilitating apparatus according to claim 2, wherein each of the first and second submandibular gland massaging devices includes:
   a fourth step motor;
   a rotation plate which is rotated in connection to the fourth step motor;
   a second massaging member which massages a submandibular gland; and
   a connection member of which the one side is connected to a position shifted from the center of the rotation plate and of which the other side is connected to the second massaging member.

4. The automatic salivation facilitating apparatus according to claim 3, wherein each of the first and second submandibular gland massaging devices further includes
   a second contact portion which is disposed in front of the second massaging member and is configured with a disposable cover made of a waterproof material so that the second contact portion is replaced after the use of the automatic salivation facilitating apparatus.

5. The automatic salivation facilitating apparatus according to claim 1, wherein the first massaging member includes:
   a connection bar of which the one side is connected to the surface of the conveyor; and
   a rotation ball which is disposed to the other side of the connection bar.

6. The automatic salivation facilitating apparatus according to claim 5,
   wherein each of the first and second parotid gland massaging devices further includes a second step motor which is arranged between the first massaging member and the conveyor, and
   wherein the connection bar is configured so that the one side thereof is connected to the second step motor.

7. The automatic salivation facilitating apparatus according to claim 5,
   wherein the connection bar is made of an elastic member, and
   wherein the rotation ball is formed in one of semispherical and spherical shapes.

8. The automatic salivation facilitating apparatus according to claim 1, wherein each of the first and second parotid gland massaging devices further includes a first contact portion which is disposed in front of the first massaging member and is covered with a disposable cover made of a waterproof material.

9. The automatic salivation facilitating apparatus according to claim 1, wherein the salivation agent injection unit includes:
   a salivation agent syringe which is configured to include a cylinder which contains a salivation agent and where an outlet for ejecting the salivation agent is formed at the one side thereof and a plunger which is moved along an inner side of the cylinder;
   a third step motor;
   a gear mechanism which is configured to include a primary gear which is connected to the third step motor and a plurality of secondary gears which are moved in engagement with the primary gear;
   a plunger moving screw which is rotated in connecting to the last secondary gear in the gear mechanism;
   a plunger gasket which is disposed in an inner portion of the cylinder of the salivation agent syringe and disposed to the one side of the plunger to adjust an internal pressure of the cylinder according to the movement the plunger gasket; and
   a plunger fastening nut which is disposed to the other side of the plunger opposite to the plunger gasket and is moved in engagement with the rotation of the plunger moving screw to move the plunger, so that the salivation agent injection amount can be adjusted.

10. The automatic salivation facilitating apparatus according to claim 9, wherein the salivation agent injection unit includes a salivation agent injection tube of which the one side is connected to the outlet of the salivation agent syringe and of which the other side is disposed in a user's oral cavity and which is configured with a flexible material.

11. The automatic salivation facilitating apparatus according to claim 10, wherein the salivation agent injection unit further includes an injection tube fastening member which fastens the salivation agent injection tube to the user's oral cavity, and
   wherein the injection tube fastening member is fixed to user's teeth.

12. The automatic salivation facilitating apparatus according to claim 1,
   wherein the control unit further includes an external setting unit which can set operation conditions externally, and
   wherein the control unit is operated according to the conditions set by the external setting unit.

13. The automatic salivation facilitating apparatus according to claim 1, wherein the automatic salivation facilitating apparatus further includes a third fixing member which connects the first and second parotid gland massaging devices and is disposed at a predetermined angle with respect to the first fixing member.

* * * * *